United States Patent
Kotik et al.

(10) Patent No.: US 7,454,855 B2
(45) Date of Patent: Nov. 25, 2008

(54) IDENTIFICATION BAND WITH DETACHABLE MACHINE-READABLE LABELS

(75) Inventors: Mark M. Kotik, Santa Monica, CA (US); Dean D. Peterson, Sylmar, CA (US); Walter W. Mosher, Jr., West Hills, CA (US)

(73) Assignee: Precision Dynamics Corporation, San Fernando, CA (US)

( * ) Notice: Subject to any disclaimer, the term of this patent is extended or adjusted under 35 U.S.C. 154(b) by 135 days.

(21) Appl. No.: 11/427,054

(22) Filed: Jun. 28, 2006

(65) Prior Publication Data

US 2007/0028495 A1    Feb. 8, 2007

Related U.S. Application Data

(63) Continuation-in-part of application No. 10/699,493, filed on Oct. 30, 2003, now abandoned.

(51) Int. Cl.
*A44C 5/00* (2006.01)
(52) U.S. Cl. .................................................... 40/633
(58) Field of Classification Search ................ 40/633, 40/6; 283/75, 900; 63/3, 3.2
See application file for complete search history.

(56) References Cited

U.S. PATENT DOCUMENTS

| | | | | |
|---|---|---|---|---|
| 3,660,916 | A | * | 5/1972 | McDermott et al. ........... 40/633 |
| 3,698,383 | A | | 10/1972 | Baucom |
| 3,751,835 | A | * | 8/1973 | Smith ........................... 40/633 |
| 4,134,320 | A | | 1/1979 | Oya |
| 4,145,966 | A | | 3/1979 | Peterson et al. |
| 4,221,063 | A | | 9/1980 | Charles et al. |
| 4,311,740 | A | | 1/1982 | Kay |
| 4,476,381 | A | * | 10/1984 | Rubin .......................... 235/375 |
| 5,071,168 | A | | 12/1991 | Shamos |
| 5,364,133 | A | * | 11/1994 | Hofer et al. .................... 283/75 |
| 5,448,846 | A | | 9/1995 | Peterson et al. |
| 5,479,797 | A | | 1/1996 | Peterson |
| 5,609,716 | A | | 3/1997 | Mosher, Jr. |
| 5,615,504 | A | | 4/1997 | Peterson et al. |
| 5,653,472 | A | | 8/1997 | Huddleston et al. |
| 5,792,299 | A | | 8/1998 | Mosher |
| 5,799,426 | A | | 9/1998 | Peterson |
| 5,973,600 | A | | 10/1999 | Mosher, Jr. |
| 5,979,941 | A | | 11/1999 | Mosher, Jr. et al. |
| 6,067,739 | A | | 5/2000 | Riley |

(Continued)

*Primary Examiner*—Gary C Hoge
(74) *Attorney, Agent, or Firm*—Kelly Lowry & Kelley, LLP

(57) ABSTRACT

An improved identification band such as a wristband is provided for mounting onto a specific person or object. The improved identification band includes a primary identification zone adapted to receive human-readable and/or machine readable information as by printing and/or programming of a radio frequency identification (RFID) circuit. The band further includes multiple detachable adhesive labels forming a portion of the band and multiple detachable cards forming a tail end extension thereof, wherein each label is adapted to receive human-readable and/or machine readable information as by printing and/or programming of a radio frequency identification (RFID) circuit. In use, such as when worn by a patient in a hospital or the like, the detachable labels and cards are individually separable from the identification band on an as-needed basis for association with other objects associated with the band wearer, such as a vial containing a patient blood sample or the like.

6 Claims, 4 Drawing Sheets

U.S. PATENT DOCUMENTS

| | | |
|---|---|---|
| 6,100,804 A | 8/2000 | Brady et al. |
| 6,438,881 B1 | 8/2002 | Riley |
| 6,510,634 B1 | 1/2003 | Riley |
| 2001/0115553 | 8/2001 | Rodriguez et al. |
| 2003/0173408 A1 | 9/2003 | Mosher et al. |
| 2004/0056769 A1 | 3/2004 | Peterson |
| 2004/0113421 A1 | 6/2004 | Penuela et al. |
| 2004/0130143 A1 | 7/2004 | Valenti, Jr. |

* cited by examiner

IDENTIFICATION BAND WITH DETACHABLE MACHINE-READABLE LABELS

BACKGROUND OF THE INVENTION

This invention relates generally to improvements in identification band appliances such as wristbands and the like for mounting onto a specific person or object, and for carrying information associated with the specific band wearer. More particularly, this invention relates to an improved identification band incorporating a primary identification zone in combination with a plurality of detachable or peel-off adhesive labels and a plurality of detachable cards, wherein the primary identification zone, each detachable label and each detachable card is adapted to receive human-readable and/or machine readable information as by printing and/or programming of a radio frequency identification (RFID) circuit. The invention is particularly suited for use as a wristband or the like to be worn by a patient in a hospital or other medical facility, wherein patient information can be inputted to the wristband, labels and cards at a convenient time such as at the time of patient admission or thereafter, with the information-bearing labels and cards being subsequently and individually separable from the identification band on an as-needed basis for adherence to other objects associated with the patient, such as a vial containing a patient blood sample or the like.

Identification bands such as wristbands or bracelets and the like are commonly used to identify individual patients in a hospital or other medical facility. The identification band is normally imprinted with patient identification information such as patient name, room number, patient identification (ID) number, etc., and then secured about the patient's wrist or the like at the time of admission to the medical facility. Thereafter, in the course of patient treatment, the identification band is used to confirm and verify patient identity thereby insuring that each specific patient receives the appropriate treatment, pharmaceuticals, laboratory tests, surgical procedures, etc. In many instances, facility protocol will require transcribing of certain patient information onto other medical forms and/or objects such as specimen-containing vials and the like. Unfortunately, human transcription errors can still occur.

A variety of improved patient identification systems and methods have been developed in an attempt to provide improved correlation between a specific patient, and corresponding medical forms and laboratory specimens and related test results and the like. By way of illustrative example, a multi-part form has been provided to include a printable patient identification band such as a wristband, in combination with one or more printable adhesive labels, wherein the wristband and labels are concurrently imprinted with appropriate patient information, for example, at the time of patient admission to a medical facility. Further improvements include removable cards imprinted with the same information. The identification band is then detached from the multi-part form and secured to the associated patient. The related label and card portions of the multi-part form are then typically retained with the patient's chart or file, where the pre-printed labels and cards are available for individual detachment and affixation to subsequent medical forms, specimen vials and the like on an as-needed basis. See, for example, U.S. Pat. Nos. 4,122,947; 5,653,472; 6,067,739; 6,510,634; and 6,438,881; and copending U.S. Ser. No. 10/322,320.

While the above-described multi-part form system and method beneficially reduces or eliminates transcription errors, there is an inherent requirement to separate the pre-printed labels and cards from the patient identification band. As a result, when it is desired to affix one of the pre-printed labels onto a subsequent medical document or object, it is essential for medical personnel to retrieve and use a correct label associated with a specific patient. However, since medical personnel are commonly required to work concurrently with several patients at any given time, a significant opportunity remains for human error in connection with affixing an incorrect label or card associated with a different patient to medical documents and objects.

There exists, therefore, a continuing need for further improvements in and to patient identification bands and associated pre-printed label and card systems, for insuring substantially fail-safe affixation of a correct label or card associated with a specific patient to subsequent medical forms and documents, and related medical devices such as laboratory containers and the like. The present invention fulfills these needs and provides further related advantages.

SUMMARY OF THE INVENTION

In accordance with the invention, an improved identification band such as a wristband is provided for mounting onto a specific person or object, wherein the identification band incorporates a primary identification zone, a plurality of detachable adhesive labels and a plurality of detachable cards. The primary identification zone, one or more of the detachable labels, and one or more of the detachable cards are adapted to receive human-readable and/or machine readable information associated with the specific wearer, as by printing and/or by programming of a radio frequency identification (RFID) circuit. In use, such as when worn by a patient in a hospital or the like, the detachable labels and cards are individually separable from the identification band on an as-needed basis for association with other objects associated with the band wearer, such as a medical form or a laboratory vial containing a patient blood sample or the like.

In a preferred form, the identification band comprises an elongated strap having a head end and a tail end sized to wrap comfortably and adjustably about a target portion of a specific person or object, such as a wristband wrapped about the wearer's wrist. The head and tail ends include and/or are adapted for assembly with fastener means for securing the band about the wearer with a selected diametric size. Exemplary fastener means are shown and described in U.S. Pat. No. 5,448,846, which in incorporated by reference herein.

The band includes the primary identification zone preferably comprising an outwardly visible region for receiving and visibly bearing selected information associated with the band wearer. Such wearer-associated information may comprise printed human-readable information such as name and other identifying data, and/or printed machine-readable information such as information codes, bar codes, etc. In addition, in accordance with one preferred form of the invention, the primary identification zone may include an RFID circuit or chip adapted for programmable reception of wearer-associated information which can be subsequently communicated with a remote reader. Such wearer-associated information inputted to the RFID circuit or chip may be updated and/or changed, if and as necessary.

The band further includes the plurality of detachable labels each bearing the same or selected portions of the wearer-associated information carried by the above-described primary identification zone. That is, each label may carry printed human-readable and/or machine-readable information, and/or an RFID circuit or chip. Once again, wearer-associated information inputted to each RFID circuit or chip may be updated and/or changed, if and as necessary. In the preferred form, the multiple labels are formed on a face ply of the band, with each label having an underside surface carrying a pressure sensitive adhesive normally affixed to an underlying release film on a base ply. The multiple labels are formed in a convenient array according to the size and shape of the band, such as an end-to-end series array, with appropriate die cuts formed therebetween to permit an individual label to be detached when desired from the identification band, without removing the band from the wearer, whereupon the detached label can be affixed substantially immediately to the desired document or object to be associated with the band wearer. The labels may be formed directly on the band strip generally between or forming a portion of the head and tail ends. The band also includes the plurality of detachable cards each bearing the same or selected portions of the wearer associated information carried by the above described primary identification zone. That is, each card may carry imprinted human readable and/or machine readable information, and/or an RFID circuit or chip. Once again, wearer-associated information inputted to each RFID circuit or chip may be updated and/or changed, if and as necessary. In the preferred form, the multiple cards are formed on a face ply and base ply of the band, with each card having a portion of the face ply inseparably adhered to a corresponding portion of the base ply. The portion of the band comprising the cards does not include a release film on the base ply. The multiple cards are formed in a convenient array according to the size and shape of the band, such as an end-to-end series array, with appropriate die cuts formed therebetween to permit an individual card to be detached when desired from the identification band, without removing the band from the wearer, where upon the detached card can be associated substantially immediately with the desired document or object to be associated with the band wearer. The cards may be formed directly on the band strip generally formed on a tail end extension adapted for looped wrapping with the band when secured on the wearer's wrist or the like.

In accordance with a preferred method, the identification bands are provided with a succession of individual bands interconnected end-to-end in roll form or the like, and adapted for suitable separation by means of intervening preformed perforations or the like. The bands can be drawn one-at-a-time through a suitable print station including a print head and/or an RFID circuit programmer for inputting desired wearer-specific information to an individual identification band. The resultant information-bearing band can then be detached from the roll or the like, and then appropriately mounted onto the specific wearer's wrist or the like.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a top plan view illustrating an identification band constructed in accordance with the novel features of the invention, to include a primary identification zone in combination with a plurality of detachable labels and a plurality of detachable cards, wherein the primary identification zone and each of the detachable labels and cards are adapted to receive human-readable and/or machine-readable information correlated with a specific person or object as by printing and/or programming of an RFID chip or the like;

DETAILED DESCRIPTION OF THE PREFERRED EMBODIMENT

Figure 1:
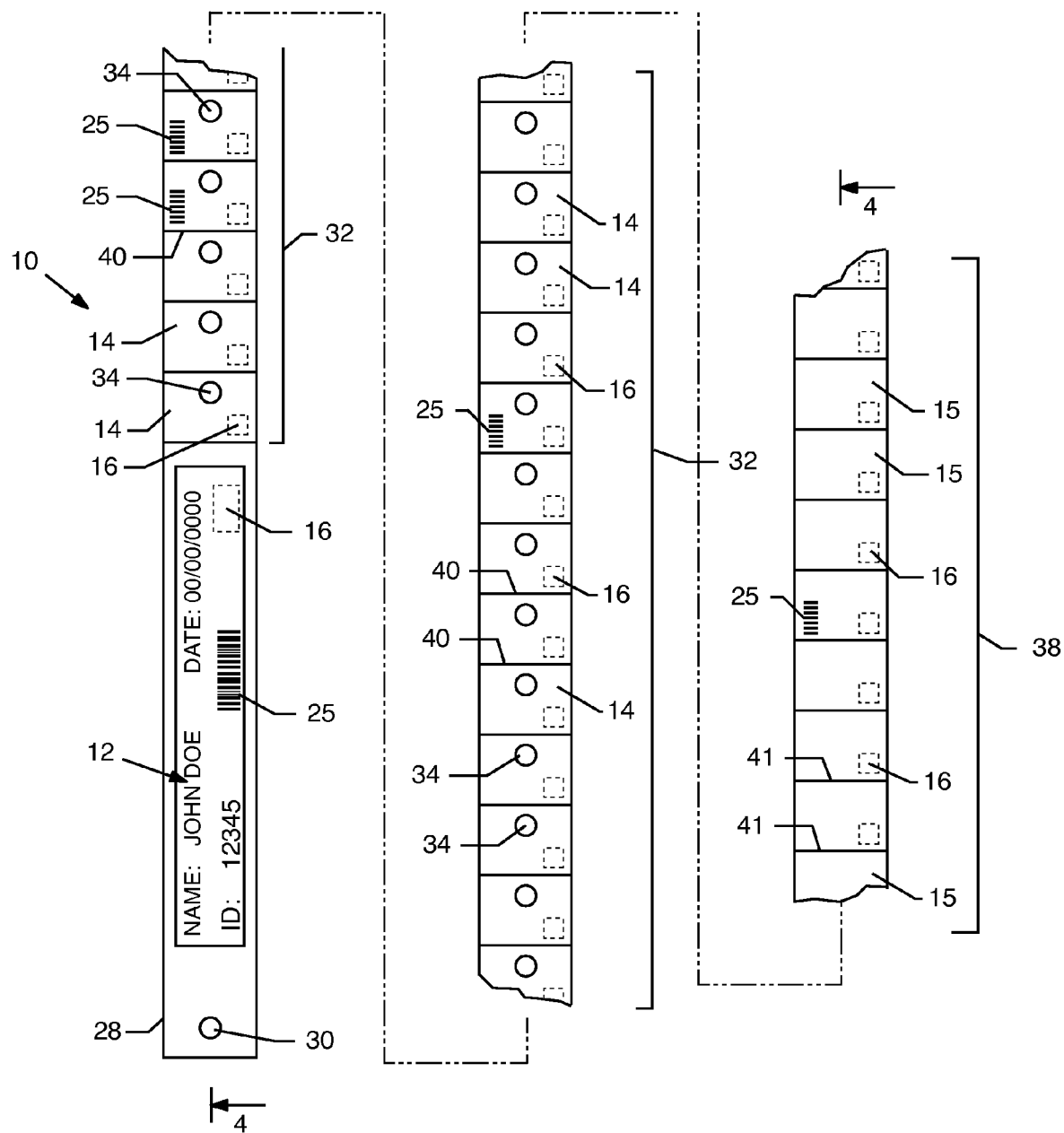
Figure 2:
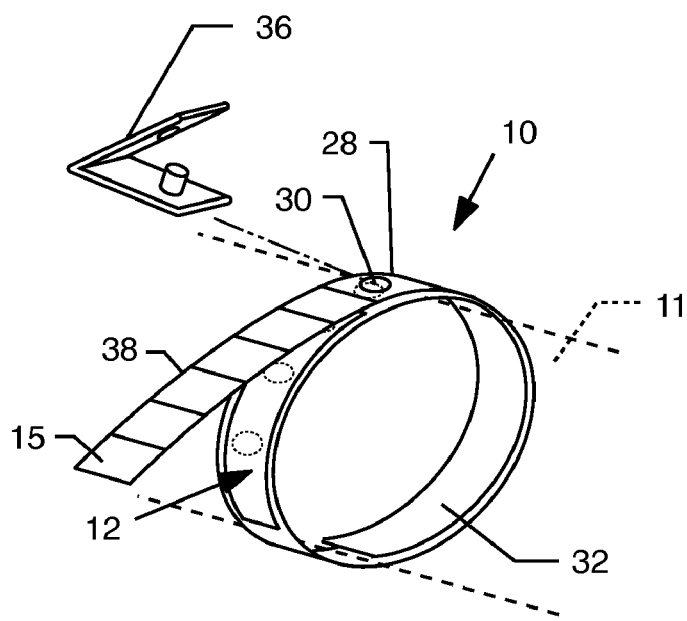
FIG. 2 is a perspective view showing wrap-around mounting of the identification band of FIG. 1 onto the wrist or the like of a person, with the identification band being depicted in exploded relation with a fastener for retaining the band on the person's wrist.
Figure 3:
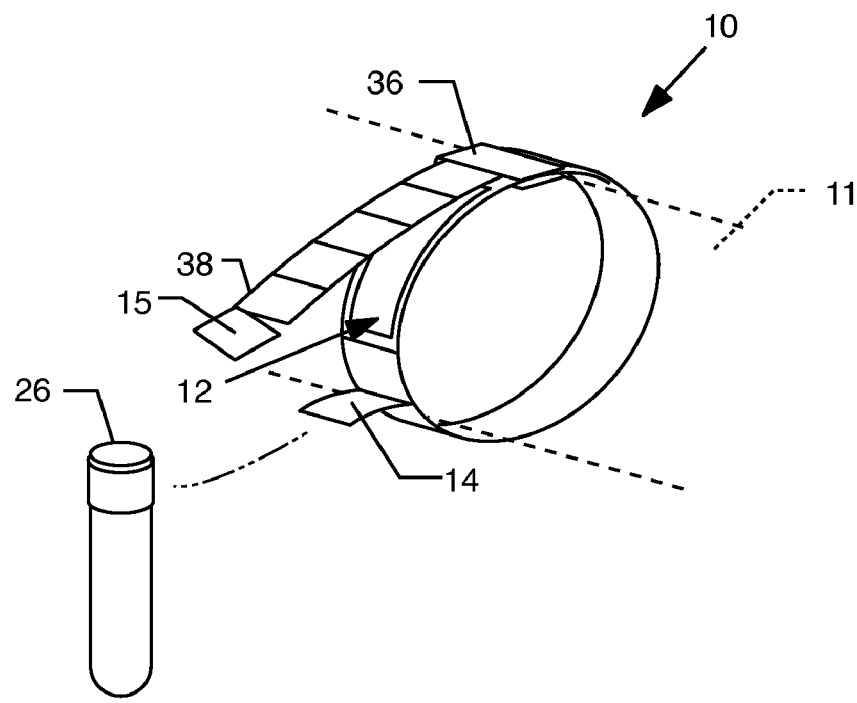
FIG. 3 is a perspective view similar to FIG. 2, but illustrating the fastener engaged with the identification band, and further depicting peel-off detachment of one label for affixation to an object to be associated with the band wearer and partial detachment of one card for association with an object.

As shown in the exemplary drawings, an improved identification band referred to generally in FIGS. 1-3 by the reference numeral 10 is provided for mounting onto a specific person or object, such as a wristband for mounting onto the wrist 11 of a patient in a medical facility or the like. The identification band 10 incorporates a primary identification zone 12 for receiving or bearing identification information associated with the specific wearer, in combination with a plurality of peel-off adhesive labels 14 and a plurality of detachable cards 15, all of which also receive or bear identification information associated with the wearer. The information can be applied to the band in human-readable and machine readable form, and preferably a combination thereof, and may additionally include programmable information inputted to a radio frequency identification (RFID) circuit or chip 16 provided on or in the primary identification zone 12 and additionally provided on or in each of the peel-off labels 14 and cards 15.

Figure 4:
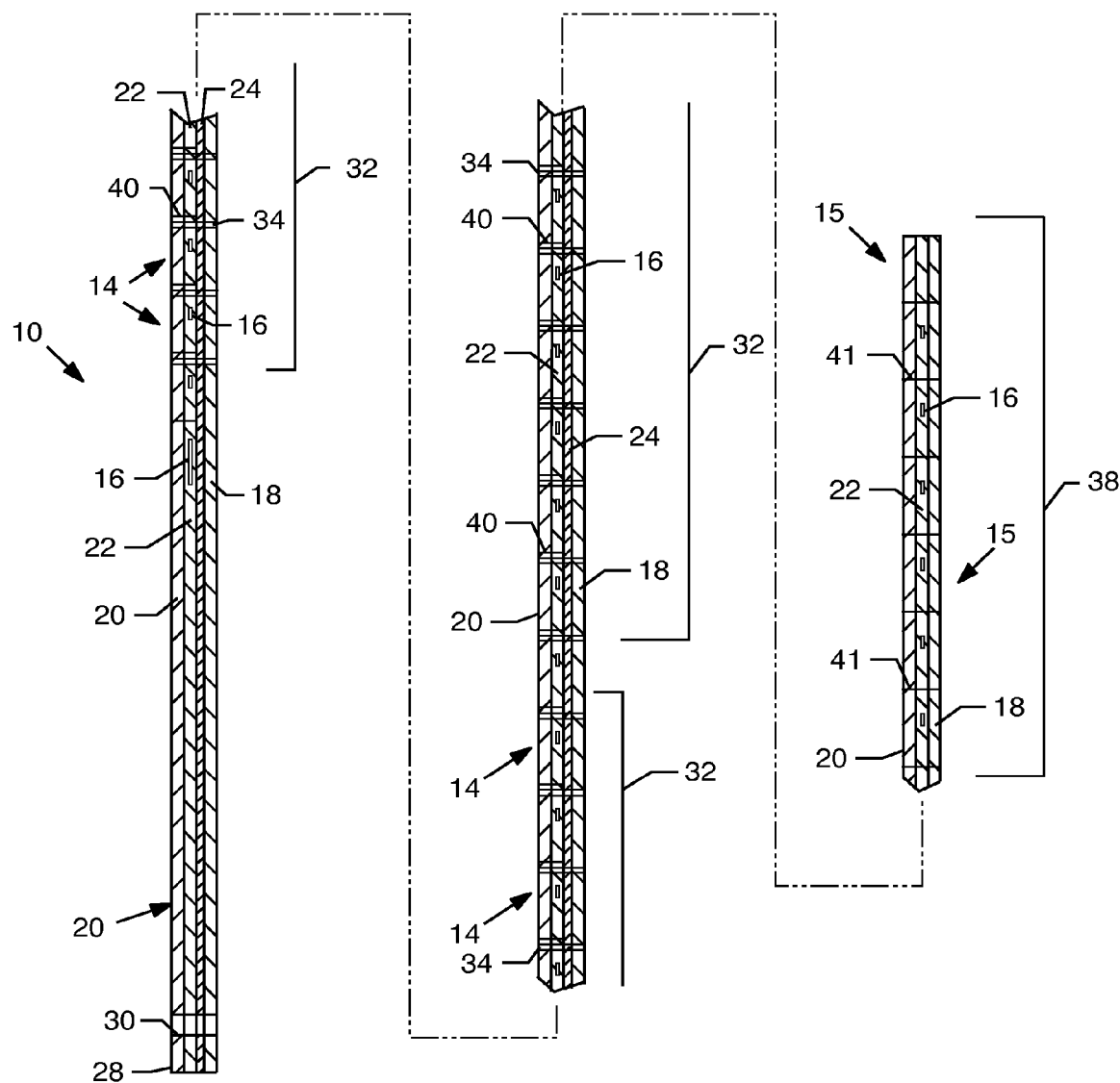
FIG. 4 is an enlarged longitudinal sectional view taken generally on the line 4-4 of FIG. 1.
Figure 5:
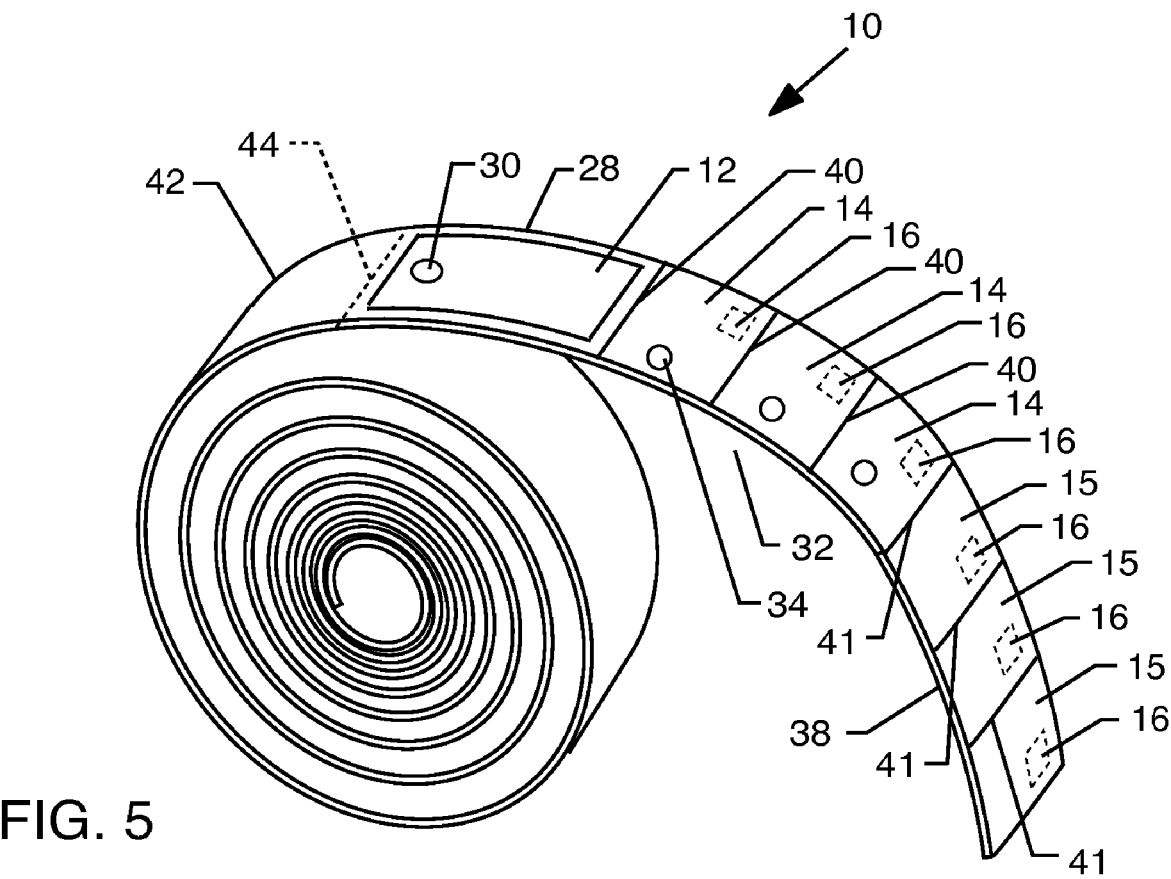
FIG. 5 is a somewhat schematic perspective view depicting a supply of identification bands of FIG. 1 detachably connected end-to-end in roll form.

The improved identification band 10 of the present invention generally comprises an elongated flexible strap formed from a suitable lightweight and flexible material such as a selected plastic or paper-based material which is preferably resistant to significant longitudinal stretching. In general terms, and as viewed best in FIG. 4, the band strap comprises a multi-layer laminated structure having a base ply 18 supporting an overlying face ply 20 which defines the primary identification zone 1, the multiple peel-off labels 14 and the multiple cards 15. A layer of adhesive material 22 such as a suitable pressure sensitive adhesive is carried at an underside surface of the labels 14 for quick and easy peel-off separation from a release liner or film 24 carried by the base ply 18. The same adhesive material 22 binds the face ply 20 to the base ply 18, without the release liner 24, to form the cards 15.

This identification band 10 is particularly suitable for use in a medical facility such as a hospital or the like, wherein the band 10 can be imprinted with or otherwise receive a variety of patient identification information at the time of patient admission. Such information may comprise items such as patient name, date of admission, patient identification number, and optional additional information such as patient condition or treatment regimen, etc. At least some of this patient identification information is applied as by machine printing directly onto the primary identification zone 12 of the band 10, in human readable form. Other information may be applied as by machine printing in coded form, or in machine readable form such as a bar code 25 or the like. Still further, in accordance with one preferred form of the invention, patient identification information can be inputted by as by machine printing in human or machine readable form, and by electronic programming of each RFID circuit 16 on or in the primary identification zone 12, on or in one or more of the detachable labels 14 and on or in one or more of the detachable cards 15, wherein the type and extent of information inputted to the RFID circuits 16 will be a function of circuit memory capacity. Selected patient identification information may also be applied as by printing in human-readable and/or machine-readable form to each of the detachable labels 14 and each of the detachable cards 15. For illustrative examples of identification bands and the like including RFID circuits and related programming technology, see U.S. Pat. Nos. 5,479,797; 5,493,805; 5,457,906; 5,581,924; 5,973,598; 5,973,600; 6,181,287; and 6,414,543, which are incorporated by reference herein.

In use, the information-bearing identification band 10 including the detachable labels 14 and cards 15 can be mounted quickly and easily onto the wrist 11 (FIGS. 2-3) of the specific person associated with that recorded information. Thereafter, as the patient's treatment proceeds, the identification information borne by the band 10 can be used by medical personnel to verify and confirm patient identity. Such verification/confirmation may include wireless transmission of information from the RFID circuit on the primary identification zone 12 or carried by any one of the detachable labels 14 or cards 15, by means of a remote RFID reader (not shown). In addition, when and as needed, the information inputted to the RFID circuits 16 on the band can be changed and/or updated.

In the course of treatment, a variety of medical forms and/or physical objects, such as a vial 26 (FIG. 3) containing a fluid specimen such as blood from the patient, will need to be marked for accurate correlation with the particular patient. When this need arises, one of the labels 14 bearing or carrying the pre-printed or pre-programmed patient identification information can be removed from the band 10 and then affixed directly and substantially immediately to the medical form or physical object such as the vial 26. Alternatively, one of the cards 15 bearing or carrying the pre-printed or pre-programmed patient identification information can be removed from the band 10 and then associated directly and substantially immediately with the medical form or physical object, i.e., as inserted in a pocket or associated by other means. Importantly, these identification labels 14 and cards 15 are carried by the band 10, and thus stay with the patient at all times, whereby detachment of a label 14 or a card 15 takes place without removing the band 10 from the patient. Potential mislabeling errors wherein patient information is manually written onto blank forms or labels, or wherein it is necessary to retrieve and use pre-printed labels which have been separated from the identification band or patient, are thus substantially eliminated. While the invention is shown and described herein for patient identification in a medical facility, it will be recognized and appreciated that the improved identification band 10 including the detachable labels 14 and cards 15 may be used in a variety of different identification environments.

In one preferred form as depicted in FIGS. 1-5, the elongated multi-layer or laminated strap forming the identification band 10 has a longitudinal length sufficient to wrap comfortably yet securely about the wrist 11 or the like of a specific patient, and a transverse width typically on the order of about ½ to about ¾ inch sufficient to bear the patient identification information to be applied thereto. At least one and preferably both of the base ply 18 and the overlying face ply 20 are formed from a sturdy stretch resistant material such as a suitable synthetic plastic sheeting, with the face ply 20 also being suitable for machine printing of patient identification information thereon. One end of the band 10 comprises a head end 28 shown with fastener means such as a fastener port 30 formed therein, whereas an opposite tail end 32 has adjustable fastener means such as a longitudinally spaced plurality of fastener ports 34 formed therein. The band 10 is adapted for wrap-around mounting onto the wrist 11 (FIGS. 2-3) or the like of patient, and a fastener member 36 such as a snap-fit clip or clasp is for interconnecting the band head and tail ends 28, 32 to form a closed loop of selected diametric size according to the particular tail end port 34 through which the fastener member 36 is fitted. Such fastener clips 36 are shown and described in more detail in U.S. Pat. No. 5,448,846, which in incorporated by reference herein.

A substantial portion of the external or outboard surface area of the face ply 20 defines the visibly exposed primary identification zone 12 of the band 10. This primary identification zone 12 is formed adjacent to the plurality of detachable labels 14, which in turn are formed in a suitable array that is compatible with the overall width and length of the band 10. The illustrative drawings show the primary identification zone 12 disposed in end-to-end series relation with the plurality of detachable labels 14 which, as shown, extend in turn in an end-to-end array over a portion of the band length between the primary zone 12 toward the tail end 32. In addition, the detachable cards 15 are formed on a tail end extension 38 which protrudes longitudinally beyond the tail end 32. When the card-bearing tail end extension 38 is provided as shown, this extension 38 may be wrapped circumferentially with or about the closed loop band 10 attached (as viewed in FIGS. 2-3) by the fastener clip 36 onto the wearer's wrist 11 or the like. Persons skilled in the art will recognize and appreciate the primary identification zone 12 and/or the detachable labels 14 may be oriented in alternative arrays other than the end-to-end arrays as shown.

For facilitated detachment when needed, the multiple labels 14 are associated with transversely extending die cuts 40 formed through the face ply 20, and preferably also through the layer 22 of pressure sensitive adhesive or the like carried at the underside surfaces of each label 14, but without extension of such die cuts 40 through the supporting base ply 18. With this construction, each individual label 14 can be removed quickly and easily (as depicted in FIG. 3) by peel-off separation from the release film 24 and suitable affixation onto another structure, such as the illustrative specimen-containing vial 26. The RFID circuits or chips 16 may be embedded within the band, as by locating these elements at the underside of the face ply 20 as shown, or alternately these elements may be adhered to the exterior side of the face ply 20, if desired.

Similarly, the multiple cards 15 are associated with transversely extending die cuts 41 formed through the face ply 20, the adhesive layer 22 and the base ply 18. With this construction, each individual card 15 may be removed quickly and easily (as depicted in FIG. 3) by tearing the last card 15 from the band 10 and suitably associating it with another object. The RFID circuits or chips 16 may be embedded within the band, as by locating these elements between the face ply 20 and base ply 18 as shown, or alternatively these elements may be adhered to the exterior side of the face ply 20, if desired.

To facilitate initial application of the patient identification information onto each identification band 10, a large plurality of individual bands can be formed conveniently and economically in an end-to-end array and carried on a roll 42 (FIG. 5), with adjoining bands 10 initially interconnected by a pre-cut or pre-formed perforation 44. In this regard, to simplify band construction, each roll 42 may be constructed from common sheet stock wherein the entire face ply 20 carries the underside adhesive layer 22 and the entire base ply 18, except that portion underlying the cards 15, carries the associated release film 24, as viewed in FIG. 4. In this roll form, each identification band 10 is initially in a so-called blank state, i.e., the patient identification information has not yet been applied thereto.

Figure 6:
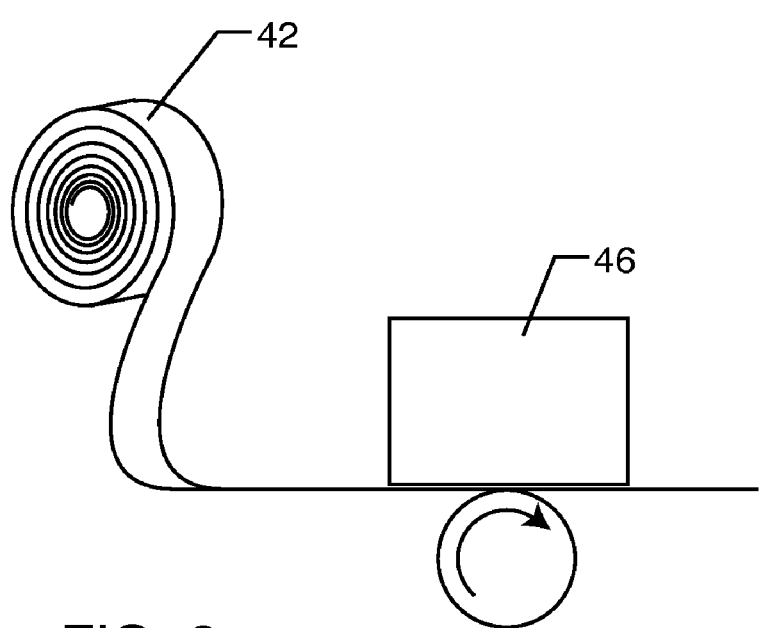
FIG. 6 is a schematic diagram illustrating a process for applying human-readable and/or machine-readable information to the primary identification zone and to each detachable label of each identification band in succession from the roll supply.

The band roll 42 is suitably mounted for feeding the identification bands 10 in succession to a print station 46 (FIG. 6) including a print head (not shown) and/or an RFID circuit programmer (also not shown) for inputting desired wearer-specific information to each individual identification band. The resultant information-bearing band 10, including the primary identification zone 12, the multiple labels 14 and the multiple cards 15, can then be detached from the roll 42, and then appropriately secured as described above onto the specific wearer's wrist 11 or the like.

A variety of further modifications and improvements in and to the improved identification band 10 of the present invention will be apparent to persons skilled in the art. Accordingly, no limitation on the invention is intended by way of the foregoing description and accompanying drawings, except as set forth in the appended claims.

What is claimed is:

1. An identification band, comprising:
    an elongated flexible strap having a head end and a tail end, and adapted for wrap-around mounting onto a specific wearer or object with said head and tail ends interconnected to form said strap into a closed loop configuration;
    a primary identification zone on said strap and adapted to receive information associated with the specific wearer or object;
    a plurality of detachable adhesive labels on said strap, said labels oriented along the strap so as to be substantially co-extensive with a portion of the strap, each of said labels being adapted to receive information associated with the specific wearer;
    a plurality of detachable cards on said strap, said cards oriented along the strap so as to be substantially co-extensive with a portion of the strap, each of said cards being adapted to receive information associated with the specific wearer;
    wherein said primary identification zone, at least one of said detachable labels and at least one of said detachable cards includes a radio frequency identification (RFID) circuit; and
    wherein said strap includes a face ply extending at least a portion of the length thereof, and a base ply underlying and supporting said face ply, said face ply defining said plurality of detachable labels removably adhered onto said base ply, and said face ply and said base ply defining said plurality of detachable cards.

2. The identification band of claim 1, further including an adhesive layer underlying each of said detachable labels and said detachable cards.

3. The identification band of claim 2 wherein said adhesive layer comprises a pressure sensitive adhesive.

4. The identification band of claim 3 further including a release film overlying said base ply, under said detachable labels.

5. An identification band, comprising:
    an elongated flexible strap having a head end and a tail end, and adapted for wrap-around mounting onto a specific wearer or object with said head and tail ends interconnected to form said strap into a closed loop configuration;
    a primary identification zone on said strap adjacent said head end thereof, and adapted to receive human-readable and/or machine-readable information associated with the specific wearer or object;
    a plurality of detachable adhesive labels on said strap, said labels oriented along the strap so as to be substantially co-extensive with a portion of the strap, each of said labels being adapted to receive information associated with the specific wearer;
    a plurality of detachable cards on said strap, said cards oriented along the strap so as to be substantially co-extensive with a portion of the strap, each of said cards being adapted to receive information associated with the specific wearer;
    wherein said primary identification zone, at least one of said detachable labels and at least one of said detachable cards includes a radio frequency identification (RFID) circuit; and
    wherein said strap includes a face ply extending at least a portion of the length thereof, and a base ply underlying and supporting said face ply, said face ply defining said plurality of detachable labels removably adhered onto said base ply, and said face ply and said base ply defining said plurality of detachable cards.

6. The identification band of claim 5 further including a layer of pressure sensitive adhesive underlying each of said detachable labels and said detachable cards, and a release film overlying said base ply under said detachable labels.

* * * * *